(12) United States Patent
Dodgson

(10) Patent No.: US 6,635,160 B1
(45) Date of Patent: Oct. 21, 2003

(54) GAS SENSOR

(75) Inventor: John Dodgson, Surrey (GB)

(73) Assignee: Central Research Laboratories Limited, Middlesex (GB)

( * ) Notice: Subject to any disclaimer, the term of this patent is extended or adjusted under 35 U.S.C. 154(b) by 0 days.

(21) Appl. No.: 09/958,105

(22) PCT Filed: Apr. 3, 2000

(86) PCT No.: PCT/GB00/01254

§ 371 (c)(1),
(2), (4) Date: Dec. 28, 2001

(87) PCT Pub. No.: WO00/60346

PCT Pub. Date: Oct. 12, 2000

(30) Foreign Application Priority Data

Apr. 1, 1999 (GB) ................................. 9907520

(51) Int. Cl.⁷ ........................ G01N 27/404; G01N 27/26
(52) U.S. Cl. ........................ 204/401; 204/412; 204/415; 204/431; 204/432
(58) Field of Search ................. 204/401, 415, 204/412, 431, 432

(56) References Cited

U.S. PATENT DOCUMENTS 2,517,382 A * 8/1950 Brinker et al.
3,003,932 A * 10/1961 Frey et al.
4,151,739 A   5/1979 Breuer et al.
4,587,003 A   5/1986 Tantram et al.
4,908,105 A * 3/1990 Garner
5,037,239 A   8/1991 Olsen et al.
5,857,460 A   1/1999 Popitz

FOREIGN PATENT DOCUMENTS

EP    0 197 257 B1   10/1986
WO    WO 98/25139 A1   6/1998

* cited by examiner

Primary Examiner—T. Tung
(74) Attorney, Agent, or Firm—Martin Fleit; Paul D. Bianco; Fleit, Kain, Gibbons, Gutman & Bongini, P.L.

(57) ABSTRACT

The invention relates to gas sensors, particularly electrochemical gas sensors. The reliability of such gas sensors has been ascertained by regular tests, which involve exposing a sensor to a gas for test or calibration purposes. However, it has been difficult to provide a known quantity or concentration of gas. Another problem has been that blockage of a gas inlet has rendered the gas sensor unreliable. The invention provides a gas sensor having a self test capability and first and second electrodes, arranged so that test gas arrives at a separate instant at each electrode so as to generate two electric currents, the ratio of which currents provides an indication of the status of at least one electrode.

4 Claims, 2 Drawing Sheets

GAS SENSOR

FIELD OF THE INVENTION

This invention relates to gas sensors, and more particularly but not exclusively, to electrochemical gas sensors.

BACKGROUND OF THE INVENTION

Electrochemical gas sensors are in common use to warn of danger from toxic gases and may be used also to warn of fire outbreak. Existing electrochemical gas sensors have not always failed safe; that is they have not indicated that they have failed, or given a signal equivalent to that from a dangerous gas concentration, when they are no longer operational.

Reliability of existing gas sensors has generally therefore only been ascertained by regular tests involving exposure to a calibration or test gas. The concentration of the test gas in the vicinity of the sensor must be known accurately and this often involves use of a considerable quantity of gas and of special methods to ensure the concentration is constant and reproducible. Particularly in fixed installations, such testing can be awkward and expensive and can necessitate temporary disabling of the system, which itself is undesirable because there is a risk that the system may not be switched on again. An electrochemical gas sensor whose function can be checked while responding to a signal gas, or with a remotely-controllable self-test capability, is therefore highly desirable.

Gas sensors with self-test by generation of a gas have been described in UK Patent GB 1,552,535 (Bayer Ltd.). The self-test sensor arrangement described comprises two elements: a sensor and a gas generation means, for example an electrolysis cell, joined to the sensor by a delivery channel. Test gas, generated by the cell, is delivered to the input of a diffusion limited gas sensor, with a membrane between the point of gas delivery and the outside world. Delivery is by a piston, a pressure difference resulting from the generation of gas itself or other means. Signal gas approaches the gas sensor from the outside world via the membrane. It is not apparent whether the membrane is intended to be a diffusion barrier, whose permeability controls the response of the sensor, or whether the membrane has a high permeability and acts mainly to prevent contamination of the apparatus by, for example, airborne dust.

In the aforementioned UK Patent, the concentration of test gas detected by the sensing electrode depends on the balance of rate of generation of the gas and the rate of loss of gas through the membrane. The latter depends on a number of conditions (including: air flow, humidity and temperature) outside the membrane. Unless a large amount of test gas is generated, or the membrane has very low permeability, the response from the sensing electrode under test depends on air flow in an undesirable way. However, a very low permeability of the diffusion barrier causes the sensor to have low sensitivity to the signal gas and so might itself be undesirable. The arrangement described in UK Patent GB 1,552,538 therefore needs a comparatively large amount of gas to give reliable operation; in turn requiring significant energy, which limits its usefulness, in particular in situations where only low power is available.

A possible failure mode of fixed installation gas sensors, incorporating the aforementioned arrangement, is that gas access from the atmosphere might become partially or completely blocked. Delivery of test gas inside the cell might result in a rise in response above that expected, as the rate of escape is reduced. However, this only becomes apparent if the sensor response is dependent entirely on the concentration of test gas inside the sensor. As the test gas is delivered directly to the sensing electrode in the aforementioned arrangement, the electrode response to the test gas is likely to be limited partially by the activity of the electrode itself, and is therefore unlikely to give a reliable indication of a blocked outer barrier.

SUMMARY OF THE INVENTION

An aim of the invention is to provide an improved gas sensor which allows reliable checks on its performance to be made and overcomes at least some of the aforementioned problems.

According to the present invention there is provided a gas sensor comprising: a sensing cell and a test cell, the test cell being arranged, so that in use, a test gas is generated on demand and a pathway is provided for directing said test gas from the test cell to the sensing cell, there being at least first and second sensing electrodes in the sensing cell, characterised in that the test gas is directed so that at least two electric currents are generated and means is provided for comparing the currents in order to provide a value indicative of the status of at least one electrode.

The life of the test gas generator depends on the amount of test gas needed in each test; this could be prohibitive in a sensor intended for long life or for frequent test if the desired amount of test gas is large. The present invention reduces considerably the amount of test gas required and makes feasible the use of small test gas generators which store small amounts of consumable substance.

Advantageously electrochemical gas generation of, and subsequent detection of, a test gas is achieved in a manner which uses less energy than previous devices.

Inclusion of a test gas generator cell and sensing cell in the same housing reduces the volume of test gas needed and hence the energy needed to power the test gas generator. Furthermore delivery of test gas between two diffusion barriers allows an increase in sensitivity above a certain threshold. This enables a warning of a blocked gas access from outside the cell to be provided.

Substantially planar cell design allows sensing and generator electrodes to be fabricated on the same substrate at a single stage. This reduces cost and allows closer spacing of components. In practice the volume of test gas required is reduced and this provides a more responsive sensor.

According to a second aspect of the present invention there is provided a sensing cell with two sensing electrodes, with gas access to the second cell via the first cell, there being a known diffusion impedance between the said cells, each cell, in use, generates an electric current, the ratio of which currents, in response to a signal gas from the atmosphere, is used to provide an indication of activity of the electrodes.

The aforementioned arrangement may be used to derive a calibration coefficient for the cell, hence maintaining its calibration beyond the point at which a conventional cell would have failed. Most importantly if the ratio reaches a predetermined value a warning of impending failure of the cell is provided. This may be activated automatically by suitable referencing means such as an integrated circuit.

Combination of a test gas generator cell and a sensor cell allows decay of the sensing electrodes to be detected using test gas when no signal gas is present. This can be used to derive a calibration coefficient. Such an embodiment is less sensitive than a conventional arrangement, or of cells with sensor and generator in the same housing, but only one sensing electrode is required. The electrode senses variations in concentration of test gas resulting, for example, from variation in performance of the test gas generator, or from variation in external air velocity, thereby allowing smaller volumes of test gas to be used, and therefore requires less energy to generate the gas.

If a second gas generator is used, which delivers gas to the second sensing electrode, together with a first gas generator which delivers gas to the first sensing electrode, each gas subsequently being able to diffuse to the other sensing electrode, then comparison of the electrode response to gas from two gas generators allows measurement of the decay of each of the two electrodes to be made. This enables an even more accurate estimate of the calibration coefficient to be made than if one generator is used alone.

Preferably sensing and generator electrodes are in the same housing and arranged so that gas is delivered from the generator electrode into a space between two diffusion barriers, the first diffusion barrier leads gas from the outside atmosphere into the space, the second barrier leads gas from this space to the sensing electrode.

According to a third aspect of the present invention there is provided a sensing cell with two sensing electrodes, with gas access to the second cell via the first cell, there being a known diffusion impedance between the said cells, each cell, in use, generating an electric current, the ratio of which currents, in response to a signal gas from the atmosphere, is used to provide an indication of the status of the cell.

In a preferred embodiment electric current is generated by a sensing electrode in response to the test gas being limited by diffusion through the second barrier. This in turn ensures that the electric current is determined by the concentration of gas in the intermediate space, and hence on the rate of diffusion of test gas from the space through the first barrier to outside the cell. If the first barrier becomes blocked by contaminants, the electric current generated in response to test gas rises. This can be used as a warning that blockage has occurred. If the second barrier were not present then electric current would depend partially on the electrode parameters and would not necessarily rise above its usual value if a blockage occurred. This preferred feature of the invention is considered to be of particular importance given the fact that gas sensors may be used in dusty environments.

The sensing cell preferably has two sensing electrodes with a connecting gas pathway therebetween. Signal gas from the outside world (atmosphere) arrives first in the vicinity of the first electrode and then (if not reacted at the first electrode) passes to the second electrode. The sensing cell contains electrolyte, a counter electrode and optionally a reference electrode. The two sensing electrodes are connected to separate current measuring devices and may be biased at either the same or different potentials, with respect to the electrolyte. Signal gas entry from the outside world to the connecting passage, is via a first diffusion barrier which controls the response of the sensing cell. Optionally a second diffusion barrier might be placed in the passage between the first and second sensing electrodes.

In normal operation, the areas and activities of the sensing electrodes and the diffusional impedance between the first and second sensing electrodes determines a proportion of the signal gas which reacts at each electrode, and hence a ratio of the currents from each. If the area of the first electrode is large and the diffusional impedance between first and second electrodes is large, most of the current will be generated at the first electrode. The sum of the currents is determined by the factors above and also by the diffusional impedance of the first (external) diffusion barrier. The current is also proportional to the external signal gas concentration. If the activity of the sensing electrodes decays, the proportion of the gas which reacts at each electrode will change—in general, the proportion at the second electrode will increase—and this will be shown by a change in the ratio of the currents.

As the electrodes decay and the current ratio changes the summed current tends to fall because gas reacting at the second electrode has diffused through a greater impedance to reach this electrode than will the gas which reacts at the first electrode. This additional diffusional impedance acts in the same way as an increase in the impedance of the external barrier in a conventional cell and the cell calibration coefficient changes. The cell therefore becomes less sensitive. However, in principle for any ratio of currents the effect of the additional impedance is known and so the new correct calibration coefficient can be found. Therefore once the cell has been calibrated initially, it can be recalibrated through the process of measurement of signal gas, even though the concentration of the signal gas is not known. Only the ratio of electrode currents is needed.

If signal gas were regularly present and there were no safety implication, then observation of the current ratio indicates correct operation of the sensor. In applications such as fixed site safety or fire monitoring, signal gas is not present except during an alarm or test procedure. Such installations are tested regularly by applying a known concentration of test gas to the sensor manually. In a particularly advantageous embodiment, the test depends only on the ratio of responses from two sensing electrodes, rather than the absolute response, so the concentration of signal gas used in the test need not be known. Therefore measures to ensure a known concentration in the vicinity of the sensor are not needed. This is advantageous for example if the detector location makes access difficult.

The sensing cell may be combined with a test gas generator in the same housing. This combination gives a self-test sensor which requires lower power and is more accurate than currently available devices.

A test gas generator cell is preferably included in the sensor housing so that a test gas generator outlet communicates with the gas space in a region adjacent the first sensing electrode in such a way that the test gas first reaches the first sensing electrode and then the second electrode. The gas generator cell may include means which liberates a controlled quantity of test gas in response to an external signal, usually electrical, e.g. an electrolysis cell which generates hydrogen from a moist electrolyte. The ratio of currents from the electrodes in response to an amount of test gas can then be used to calibrate the cell in the same way as above. The need for a known concentration of test gas in this space, mentioned above for present self-test sensors, is now relaxed, making calibration of the sensor more immune to external effects (e.g. drafts and moving air). Much smaller concentrations of test gas are required, which further reduces the power consumption.

Other preferred features of the invention are expressed in the dependent claims.

BRIEF DESCRIPTION OF THE DRAWINGS

Preferred embodiments of the invention, will now be described, by way of example only, and with reference to the Figures in which.

DESCRIPTION OF THE PREFERRED EMBODIMENTS

Operation of the invention will now be described briefly with reference to the Figures. The same principles apply irrespective of the geometric arrangement of a gas sensor cell or its components, provided that gas arrives at a first sensing electrode before it arrives at a second sensing electrode. This may be achieved in a variety of ways, though generally speaking the electrodes are disposed either horizontally (in a planar electrode arrangement, e.g. as described in the Applicants published International Patent Application No WO-A1-9825138) or vertically (in a stacked arrangement, as is well known in prior art sensors).

Figure 1A:
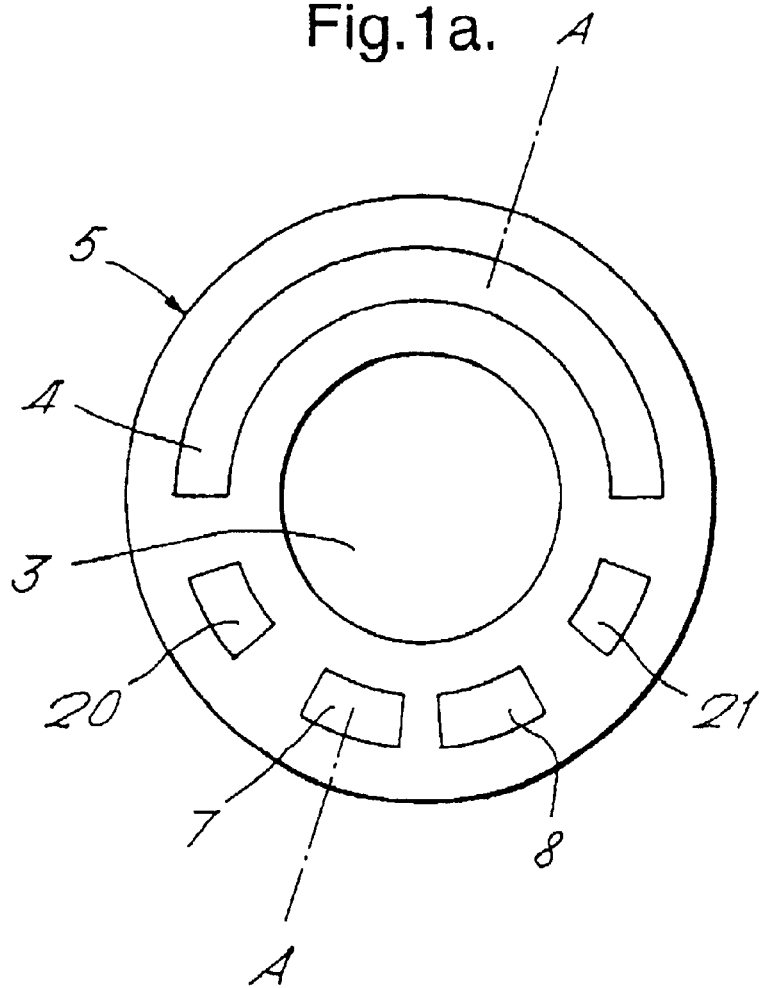
FIG. 1a shows a plan view of an electrode for use in one embodiment of sensor assembly.
Figure 1B:
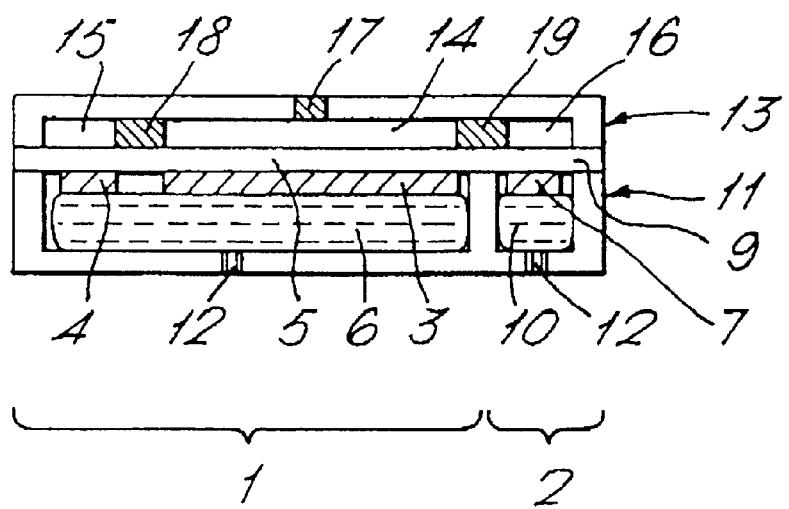
FIG. 1b is a diagrammatical, sectional view of the sensor assembly along the line A—A.
Figure 2:
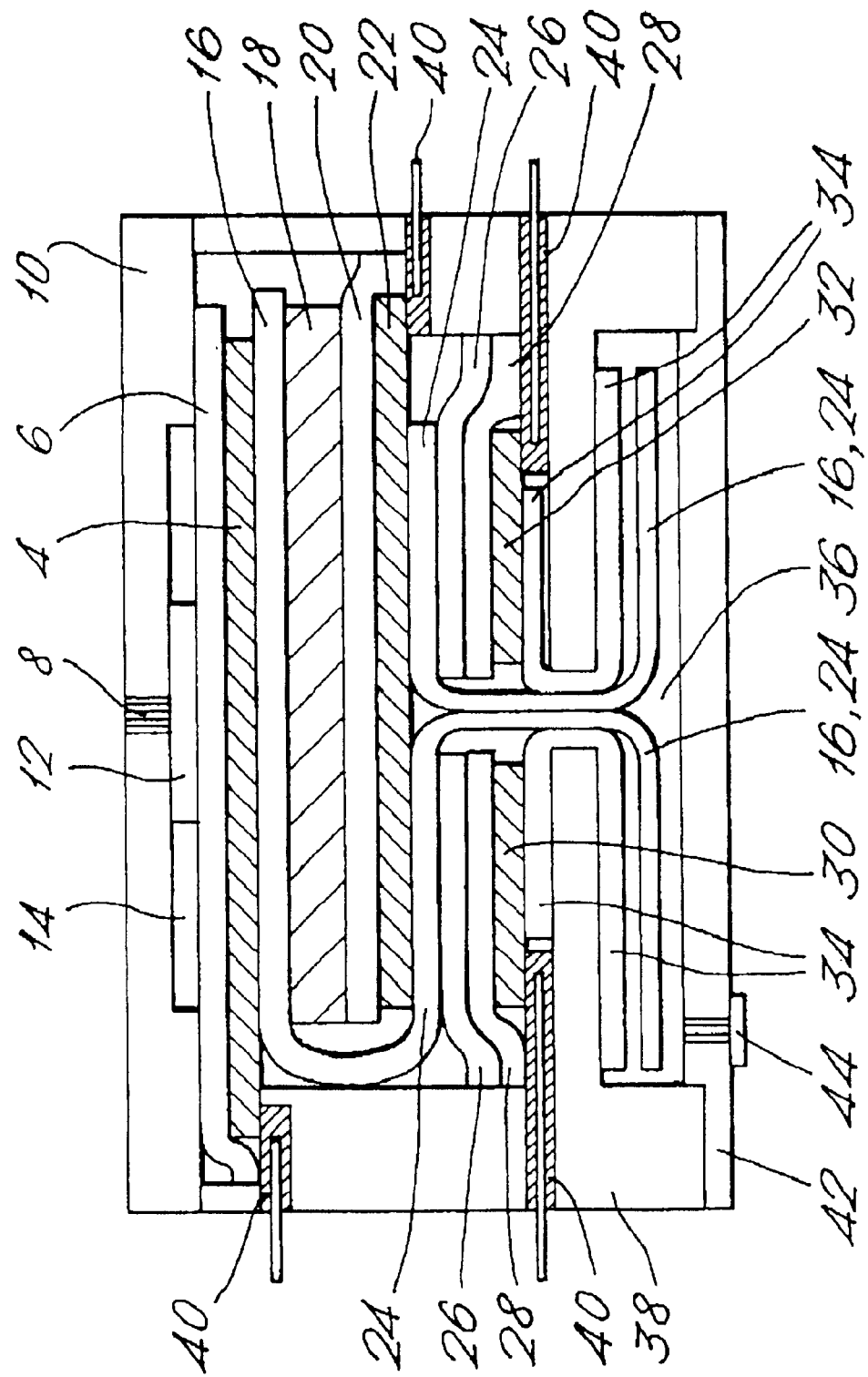
FIG. 2 is a diagrammatical sectional view of an alternate embodiment of the assembly.

The embodiment depicted in FIGS. 1a and 1b is described below. The figures show an improved sensor cell with self-test generator included in planar arrangement. An alternative embodiment is shown in FIG. 2. FIG. 2 depicts an improved sensor without test generator, in a stacked arrangement.

EXAMPLE 1

Referring to FIGS. 1a and 1b, a planar sensor with integral self-test capability for CO or similar oxidisible gas is shown in FIG. 1a, which is a plan view and FIG. 1b, which is a cross-section at A—A. A sensor comprises a sensing cell 1 and a gas generator cell 2. More than one gas generator cell may be included in the arrangement. A first sensing electrode 3 and a second sensing electrode 4 are mounted on a porous substrate 5. Electrolyte is maintained in contact with the sensing electrodes by a retaining means 6, e.g. a wick or porous matrix. A counter electrode 20 and an optional reference electrode 21 are included in the cell, also in contact with the electrolyte retainer 6, either mounted on the substrate 5 as shown in FIG. 1a or separately from it. The generator cell 2 in this example is an electrolysis cell which generates hydrogen from water in the electrolyte, though other generating means such as electrolysis of a substance in the reservoir 6 might be used to produce this or other gases. The generator cell 2 contains a hydrogen generating electrode 7 and an oxygen generating electrode 8. Electrodes 7 and 8 are mounted on a porous substrate 9 which allows hydrogen to escape from the generating cell. This substrate might be a continuation of the substrate 5 which carries the sensor cell electrodes or might be separate.

Electrolyte is maintained in contact with the generating electrodes 7 and 8 by a retaining means 10. Strong acid is preferred as an electrolyte for both sensor and generator cells as it remains wet in contact with atmospheric moisture through hygroscopicity. Substrates 5 and 9 and the electrolyte retainers 6 and 10 are held together by a plastic housing 11. A vent 12 which is permeable to gas but impermeable to electrolyte is provided in each electrolyte compartment. The electrolytes in 6 and 10 are preferably kept electrically isolated from each other; though a cell design with a common electrolyte is also capable of being within the scope of the invention.

Contact is made to the electrodes preferably by means of extending electrode material or electrical pathway through an acid-tight seal. Electrical contact may also be made using noble metal connectors led through a compressive seal, e.g. an O ring.

Cover 13 contacts substrates 5 and 9 so as to define gas spaces 14 above the first sensing electrode 3 and above the second sensing electrode 4 and above the hydrogen generator electrode. The oxygen generator electrode 8 optionally also communicates with gas space 16 or alternatively with the outside world. Access by signal gas from the outside is via one or more external diffusion barriers 17. Gas space 14 communicates with gas space 15 via an optional diffusion barrier 18 and with gas space 16 via an optional diffusion barrier 19.

Instead of the planar arrangement in example 1, gas might be arranged to flow through the first sensing electrode and thence to the second in a cell with a stacked arrangement of electrodes. Such an arrangement is shown in European Patent Application EP-A0126623 (City Technology), which shows a cell with two stacked sensing electrodes, in which gas access to the second is through the first. The electrodes are set at different potentials such that a more reactive gas is completely consumed at the first electrode while a less reactive gas passes on to the second electrode. Hence signals from the two electrodes allow the two gases to be measured selectively. The wick arrangement between the first and second electrodes in the above mentioned European Patent Application presents little diffusional impedance to the gas passing through it.

The diffusion means between the first and second sensing electrodes might be a gas space or a porous body or a thin permeable membrane. Diffusion of gas from the first to second sensing electrodes might be between the substrates, 5 and 9. In FIG. 1 if these are the same continuous material. In this case, no gas space is provided above the second sensing electrode 4. Similarly gas access from the generator electrode 7 to the sensing electrodes be through one or more continuous porous membranes 5 and 9.

The present embodiment differs from EP-A-0126623 in two key aspects: in the present invention the electrodes operate at the same potential and are intended to sense the same gas; secondly a known value of diffusional impedance is necessary between the two electrodes rather than only a gas access path, without further specification, as is disclosed by EP-A0126623.

EXAMPLES 2

FIG. 2 shows an alternative cell and omits details of sealing and contact methods. Sensing cell 1 contains a first sensing electrode 4 mounted on a porous substrate 6. Signal gas access is via the external diffusion barrier 8 located in a top cover 10. A porous membrane 12 is sealed to the barrier to prevent effects of air velocity on cell response. A space 14 allows diffusion of gas from the barrier over substantially all the top surface of the electrode. The first sensing electrode is in contact with a wick 16 which is gas-permeable, e.g. by having holes through it. Gas which does not react at the first electrode diffuses through wick 16, through a diffusion barrier layer 18, through a second porous substrate 20 to a second sensing electrode 22, where it reacts as described below. Wick 16 may be a piece of wick 24 which is in contact with the second sensing electrode 22. An optional impermeable layer 26 is placed below the wick 24 to prevent passage of gas further into the cell. A third porous substrate 28 carries a counter electrode 30 and an optional reference electrode 32, in contact with wick 34. Wicks 16, 24 (if separate from 16) and 34 are led into an electrolyte reservoir 36. The cell components are contained in a housing 38; contact is made to the electrodes by a seal process using contacts 40. The electrolyte reservoir is closed by a cap 42 with a gas permeable but electrolyte-impermeable vent 44.

The sensor will now be described in its mode of operation with reference to all the Figures. Signal gas entering the cell passes through the external barrier 17 into the space 14 from where, in normal operation, most gas diffuses rapidly through the substrate to the first sensing electrode where it is reacted. Some gas passes to space 15 above the second sensing electrode where it reacts. Therefore in normal operation of the cell there is a ratio (R) of the current from the second sensing (second) electrode divided by the current from the first electrode. The ratio (R) depends on the diffusional impedance of the gas path between the sensing electrodes, the rate of reaction at the electrodes and the area of the electrodes. The ratio (R) will be smaller the larger is the diffusional impedance between the electrodes. If the activity of the first sensing, electrode 3 falls after use, the flux of gas into it falls and the proportion of the gas passing to the second electrode 4 increases. This increases R. Two cases arise: (i) if the activity of the first electrode falls while that of the second remains constant, as might happen if the first electrode fails through poisoning by atmospheric contaminants (which can arrive at this electrode first), then R increases dramatically; (ii) if the activity of the second sensing electrode falls at the same rate as that of the first, as may occur if decay is through loss of catalytic activity or through gradual flooding of the electrode, R will again increase, but to a lesser extent. Means may be provided to distinguish between each type of change in R and to transmit a signal indicative of the difference.

In both the abovementioned cases, as the total overall diffusional impedance that the gas experiences before reaction increases, output current from the sensing electrode of the cell, for a given external concentration, will fall. The extent to which this happens is determined firstly by the impedance of the external barrier—the greater this is, the less the effect of the change through decay. Practical values of this impedance are limited by the need for a certain minimum output from the cell. If the fall in output currently of the cell is a single-valued function of the ratio of currents R then the fall can be estimated unambiguously from the ratio and the cell calibration calculated. However, the decay conditions (i) and (ii) above lead to different relations between output current (S) ratio of currents (R). As would be expected, decay of both electrodes (ii) gives a greater change in S for a given R than decay (i) of the first electrode alone. The greater the diffusional impedance between the first and second electrodes the smaller is the difference between the S and R values. The impedance and its effect depend on factors including the geometry of the cell and the ratio of the electrode areas. The inclusion of a diffusion barrier 18 in the cell allows these properties to be defined precisely.

Optimum values of diffusion impedance depend on the design of individual cells. For example, for a cell as in FIG. 1 with radius of the first sensing electrode 4 mm, inner radius of the second electrode 5 mm and outer radius 7 mm, with gas access from the atmosphere through a barrier at the centre of the first electrode, and for external barrier and internal barrier both with diffusional impedance in order to limit the current from the first electrode by a factor of 20, S can be estimated from R to within ±5% (if the first electrode decays by a factor of 7–10); or ±10% for decay by a factor 18 (if both electrodes decay—case (ii)) or by a decay factor of 10 (if only the first electrode decays—case (i)). These accuracies are usually sufficiently adequate for remote warning installations. In practice in most safety installations, any gain in sensitivity with time is less important than loss, so it is more likely that a system is set to compensate for changes in response, assuming the worse case—namely decay of both electrodes. This leads to an effective increase in sensitivity if only the first electrode has decayed, e.g. by poisoning.

For cells that include a generator as in FIG. 1, during the self-test cycle the generator cell 2 is powered for a short time to produce a pulse of gas. Electric charge passed may be sufficient to produce a steady-state signal from the two sensing electrodes, but is more likely to produce a transient signal from both electrodes. The height and integrated area of the current time response pulse is indicative of the response of the electrode and the ratio of these quantities from the two electrodes can be used to measure the state of decay of the electrodes.

More than one gas generator may be used to give optimum use of energy stored in a capacitor and optimum gas delivery to the electrode(s). Additionally, a first generator might supply gas to space 14 above the first electrode and a second generator to space 15 above the second. Gas from the second generator may then be reacted first at the second electrodes and then at the first, i.e. in an opposite sense to the gas from the first generator. Comparison of the pulse height ratios from powering the first and second generators in sequence may be used to indicate the response ratio of the electrodes, i.e. the extent to which each had decayed. This mode of operation enables the user to distinguish between decay types (i) and (ii) above and so allows accurate calibration of the sensor. Means may be provided to supply an electrical signal for any of the above mentioned functions.

A further advantage of self-testing is that test gas is delivered inside a barrier through which signal gas has to pass. Blockage of the barrier, e.g. by external contamination, is a possible mode of failure of the sensor. It is assumed from the above, that a proportion of the test gas is lost through the barrier to the outside, this proportion increases with outside air velocity to an extent which depends on barrier design. If the barrier becomes blocked the proportion will decrease below a normal threshold value in still air, and the output from both electrodes will increase, while R remains substantially constant. A response higher than a set value therefore indicates a possible blockage and the monitoring means can then give warning that cleaning or replacement may be needed.

Preferably one or more generator electrodes are disposed in the same housing in contact with either the same or separate electrolytes, at least one further electrode is in contact with each electrolyte, so that test gas from the generator electrode(s) is delivered into the space between the first sensing electrode and the first diffusion barrier.

There is also provided, within the scope of the invention, a gas sensor system including at least one of the aforementioned gas sensors, one or more electrical pathways to a control unit which monitors the state of the, or each, sensor and an alarm arranged to trigger in a response to a signal from a gas sensor.

The invention has been described by way of examples only and variation to the embodiments may be made without departing from the scope of the invention.

What is claimed is:

1. A gas sensor and testing system, comprising a gas sensor including a housing, a first external diffusion barrier mounted in a wall of the housing through which sample gas is introduced into the housing, a spaced defined in the housing in communication with the first external diffusion barrier, a first sensing electrode mounted in said housing in communication with said space, a second sensing electrode mounted in said housing spaced from the first sensing electrode, a second diffusion barrier interposed between the first sensing electrode and second sensing electrode characterized by a predetermined diffusion impedance, to define a gas pathway such that sample gas encounters the first sensing electrode before encountering the second sensing electrode, and a testing system comprising means for monitoring the electric currents and/or the areas under the current-time response pulse produced by the first and second sensing electrodes in response to a sample gas introduced via the first external diffusion barrier, wherein the testing system responsive thereto determines the ratio between the electric currents and/or areas under the current time response pulse of the first and second sensing electrodes, and thereby the condition of one or both sensing electrodes.

2. A gas sensor and testing system as claimed in claim 1 including a control unit for detecting a fault condition when the ratio exceeds a predetermined value.

3. A gas sensor and testing system as claimed in claim 1 wherein a test gas inlet is provided which bypasses the first external diffusion barrier, and a second gas pathway is defined in the housing leading from the test gas inlet serially to the first and second sensing electrodes such that test gas is exposed to said first sensing electrode before exposure to said second sensing electrode, and wherein there is further provided means for monitoring the electric currents and/or the areas under the current-time response pulse produced by the first and second sensing electrodes in response to exposure to either the sample gas introduced via the external diffusion barrier or a test gas introduced via said test gas inlet.

4. A gas sensor and testing system as claimed in claim 3 in which the gas sensor and the testing system are integrated into a common housing.

* * * * *